(12) United States Patent
Eberhard et al.

(10) Patent No.: US 6,352,181 B1
(45) Date of Patent: Mar. 5, 2002

(54) MEDIA DISPENSER WITH SNAP ACTION JOINT AND METHOD FOR MOUNTING A RESERVOIR

(75) Inventors: Thomas Eberhard, Radolfzell; Anton Breyer, Gaienhofen, both of (DE)

(73) Assignee: Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/654,626

(22) Filed: Sep. 5, 2000

(51) Int. Cl.$^7$ ................................................. B67D 5/32
(52) U.S. Cl. ............................... 222/153.13; 222/402.11
(58) Field of Search ........................ 222/153, 153.13, 222/153.14, 402.11

(56) References Cited

U.S. PATENT DOCUMENTS

| | | | | |
|---|---|---|---|---|
| 4,024,995 A | * | 5/1977 | Landen deceased et al. | 222/402.11 |
| 4,162,746 A | * | 7/1979 | Anderson et al. | 222/153.13 |
| 4,479,589 A | | 10/1984 | Ford | 222/153 |
| 4,524,888 A | | 6/1985 | Tada | 222/153 |
| 4,565,302 A | * | 1/1986 | Pfeiffer et al. | 222/153 |
| 4,934,568 A | * | 6/1990 | Fuchs | 222/153 |

FOREIGN PATENT DOCUMENTS

| | | |
|---|---|---|
| DE | 35 44 985 A1 | 6/1987 |
| DE | 89 15 554.8 | 11/1990 |
| DE | 44 00 813 A1 | 8/1994 |
| DE | 44 12 041 A1 | 10/1995 |
| DE | 196 10 457 A1 | 9/1997 |
| DE | 198 40 723 A1 | 3/2000 |
| EP | 0 194 417 A2 | 9/1986 |
| EP | 0 779 106 A2 | 6/1997 |
| WO | WO 93/03857 | 4/1993 |
| WO | WO 95/00253 | 5/1995 |

* cited by examiner

Primary Examiner—Philippe Derakshani
Assistant Examiner—Thach H Bui
(74) Attorney, Agent, or Firm—Quarles & Brady LLP

(57) ABSTRACT

A locking ring (30) is provided for assisting axial insertion and snap fit of an actuating head (5), including a pump (7), to a medium reservoir base (6) while protecting the pump (7) against actuation or excessive forces encountered during assembly. The locking ring (30) can be disengaged to allow actuation of the pump (7) and then re-engaged to permit actuation.

21 Claims, 2 Drawing Sheets

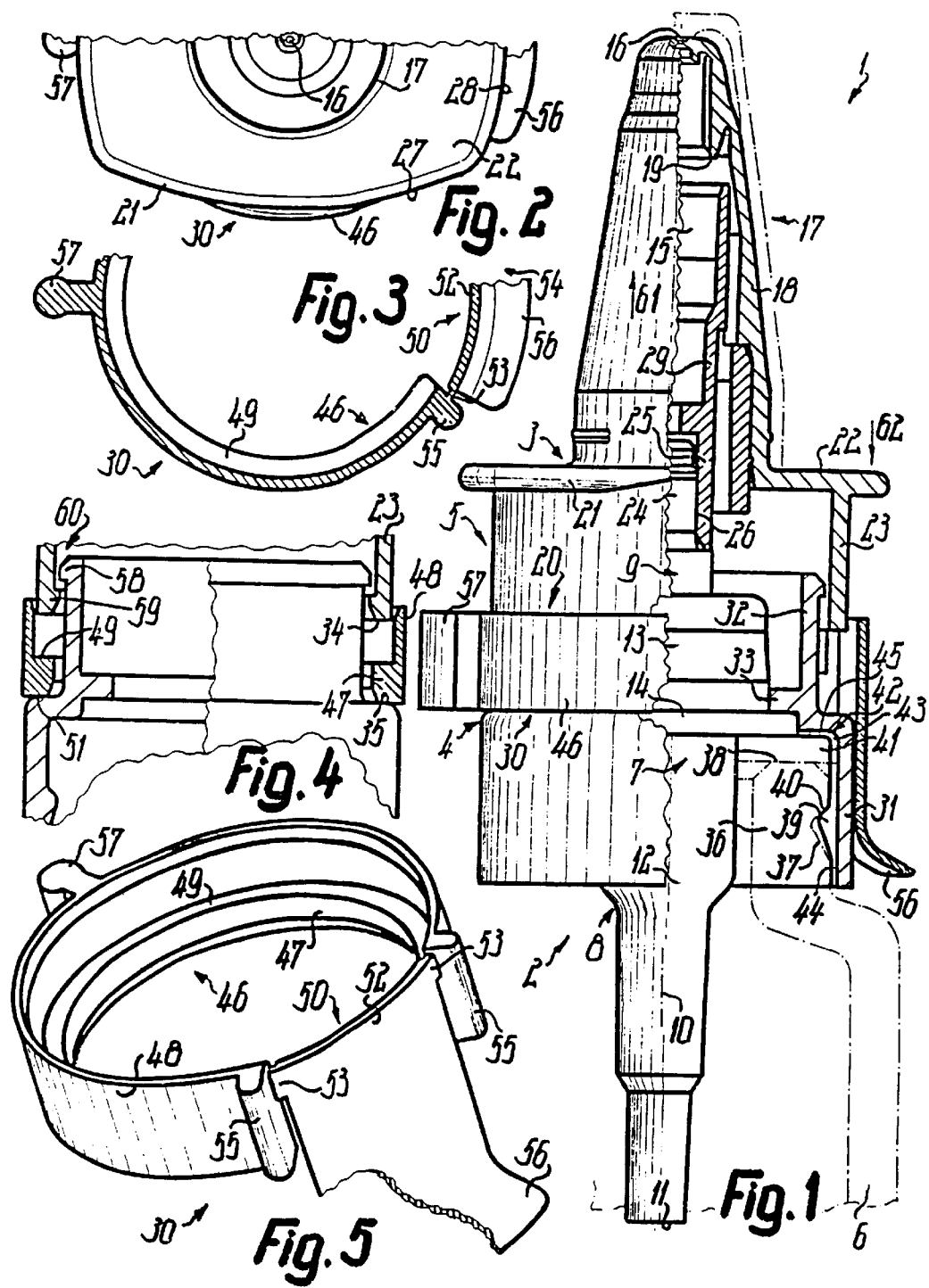

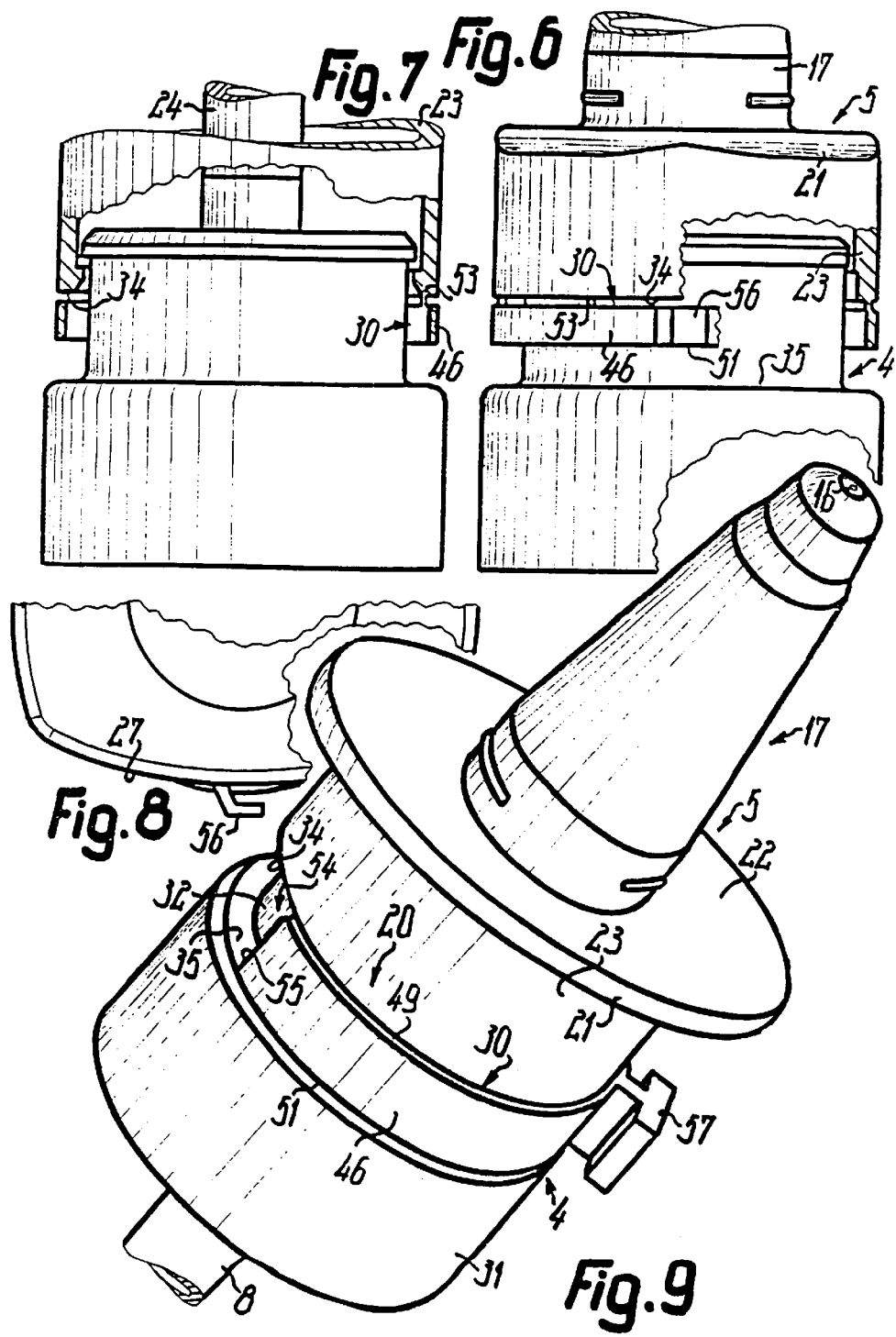

US 6,352,181 B1

MEDIA DISPENSER WITH SNAP ACTION JOINT AND METHOD FOR MOUNTING A RESERVOIR

TECHNICAL FIELD AND BACKGROUND OF THE INVENTION

The invention relates to a dispenser for media for securing to a support such as a reservoir or cylinder receptacle, a helve or the like with a mounting flange. The dispenser may comprise a volumetrically variable medium or pressure space such as a pump chamber from which the fluid medium such as a liquid, paste or cream, powder or gas can be conveyed under pressure to a medium outlet by moving a discharge and/or actuating head relative to the flange over a working stroke.

When securing the dispenser with the flange by a rotative, linear or axial movement, oriented jointing forces are necessary corresponding to a jointing resistance. The forces may increase sharply during fastening until the securing seat is attained. This seating may be a rigid or movable connection. For actuating the dispenser running forces are needed which are usually required to be introduced into the head and which likewise may increase commonly with the actuating path. The running forces correspond to a running resistance given by e.g. friction between piston and cylinder, by the resiliency of a return spring, or by the forces needed to actuate one or more valves etc.

The running resistance should be smaller than the jointing resistance. Therefore the head should not be loaded by the jointing force to avoid actuation of the head during jointing up to abutment on a stop or until the end position is attained. This stop can be encapsulated within the dispenser and may act on a counterstop of the piston unit, such as the end face of an elastic piston skirt which movably bounds, i.e. alters the volume of, the medium chamber. When this counter-stop is loaded with the jointing force it may be damaged or become leaky. Even in the absence of jointing forces it may be practical to prevent actuation up to the stop, despite the running force being fed into, e.g. as a tamperproof safeguard, childproof safeguard or the like.

OBJECTS OF THE INVENTION

An object of the invention is to overcome the disadvantages of known configurations or of the kind as described. Another object is to permit blocking of actuation against actuating forces substantially higher than any of the cited resistances. A further object is that the jointing force is not to be introduced partly or exclusively via the flange but via the head. Still another object is to permit the dispenser to be repeatedly translated into the blocked and unblocked states. A still further object is that the dispenser is straightforward in design and actuation.

SUMMARY OF THE INVENTION

The invention provides an apparatus which make it possible to join the head to the reservoir by a snap action joint without subjecting the dispenser to the snap action force. A blocking member and an actuating head, including a pump, are assemble to a medium reservoir while protecting the pump against actuation or excessive forces encountered during assembly. The blocking member can be disengaged to permit actuation.

A blocking member of the blocking means may be provided as a spacer between head and flange.(When the blocking means or its blocking member is reengaged after disegagement blocking of the actuation is repeatable.) In this arrangement the blocking member may be permanently mounted on the dispenser or totally separable from the dispenser.

The blocking member may prevent a dispenser body from being distended, for example by forming an outer shield or clamp which reinforces the dispenser body against being radially deformed.

The blocking member can be disengaged or engaged by spring forces so that it reliably holds on simple actuation. The associated actuating forces are oriented transverse to the operational and joining forces, and although the operation and joining forces may differ in direction, preferably they are parallel.

Preferably the blocking member covers a recess such as an annular gap between blocking faces to keep out dirt. The dispenser thus presents smoother outer surfaces in the blocked condition than in the unblocked condition.

The blocking member may be disengaged or engaged for securing the head to the actuating stem of the pump. The jointing forces needed to secure the head to the actuating stem are higher than the running force and may be higher or lower than the jointing forces of the flange.

The configuration according to the invention is particularly suitable for fasteners or closures including snap members, bayonet members or other rotary lock members as well as for fastening pumps having a body integral with or separate from the flange. Such pumps may be configured e.g. in accordance with the U.S. patent application Ser. No. 09/387124 to the features and effects of which reference is made for incorporating them in the invention.

BRIEF DESCRIPTION OF THE DRAWINGS

Example embodiments of the invention are explained in more detail in the following and illustrated in the drawings in which:

FIG. 1 is a partially cross-sectional view of the dispenser according to the invention, FIG. 2 is a top view of the dispenser of FIG. 1, FIG. 3 is a diametral cross-section through the blocking member of FIG. 1, FIG. 4 is an axial cross-section of FIG. 1, FIG. 5 is a perspective view of the blocking member, FIG. 6 illustrates a further embodiment as in FIG. 1, FIG. 7 is an axial cross-section of FIG. 6, FIG. 8 is a top view of FIG. 6, and FIG. 9 illustrates a third embodiment in a perspective view.

DETAILED DESCRIPTION

In FIG. 1 the dispenser 1 includes two units 2, 3 mutually movable over a working or discharge stroke. Each unit has a base or dispenser body, namely a flange 4 and a head 5. Unit 2 is fixedly connected to a base 6 or medium reservoir. Unit 2 includes a casing 8 of a pump 7 such as a thrust piston pump. The piston unit 9 of pump 7 is slidingly displaceable within casing 8. Unit 3 includes unit 9 which has within casing 8 an outlet valve. This valve has two mutually movable valve members. Piston unit 9 has a piston skirt abutting at the end of the working stroke against an inner shoulder of casing 8 to thus open the outlet valve. All parts are located in a base axis 10. Casing 8 comprises a longer sleeve-shaped housing part 12 protruding into reservoir 6. The outer end of casing 8 includes a cover 13 sealingly snapped onto part 12 or made in one part with housing part 12. The inner end of casing 8 is made to provide a medium inlet 11 followed in flow direction 61 by an inlet or ball valve located within housing part 12. Cover 13 has a radially projecting ring or disk-shaped pump flange 14 which is to be sealingly supported or tension-mounted on base 6.

Head 5 is traversed by an outlet duct 15 ending in a medium outlet 16 and porting to the environment. Outlet 16 may be an atomizer nozzle, a jet nozzle or a droplet dispenser. Outlet 16 traverses the free end of a freely protruding stud 17 suitable for nostril insertion. Instead of being located in axis 10 the medium outlet 16 may also be oriented transverse or perpendicular to axis 10 while traversing in the jacket of head 5. Stud 17 includes an outermost shelly 18 and spaced therefrom an inner shell 19. Shell 18 translates at the rear end into a planar ring-shaped end wall 21. The outside of wall 21 forms on both sides of stud 17 a handle 22, namely pressure faces for the users fingers. A protecting cap shown in dot-dashed lines may be slipped onto stud 17 to extend up to handle 22. The circumferential face of shell 18 or of this cap and the end face of stud 17 or the end face of the cap, particularly however the handle, may form the driving face 22 in connecting dispenser 1 to base 6.

A shell 23 protrudes beyond the inside of wall 21. Shell 23 is wider than but not as long as shell 18. Cover 13 is traversed by a piston stem 24 of unit 9. A plug member like a sleeve 25 is linearly pushed onto stem 24 counter flow direction 61, namely in direction 62 up to abutment. Sleeve 25 of head 5 is firmly seated on stem 24 to thus create a connection 26 frictionally firmly seating head 5 with respect to direction 61 and positively seating head 5 with respect to direction 62 by abutting on unit 9. Stem 24 like the pump piston is centrally traversed by the outlet duct. For fixing the dispenser 1 to base 6 as well as for actuating a discharge stroke the head 5 is loaded at the driving face 22 in direction 62 by the jointing force or actuating force.

Wall 21 or handle 22 is oblong rectangular with length edges 27 and narrow edges 28 convexly curved outwards. Wall 21 is traversed by an insert 29 or filler inserted into shell 18, the filler forming plug sleeve 25. Each of bodies 4, 5, 6, 12, 13, 29 is in one part and radially or axially dimensionally rigid.

For rigidly positioning head 5 relative to flange 4 in a position between the rest position shown in FIG. 1 and the actuated end position a lock 20 is provided with a blocking member 30 engaging between bodies 4, 5 as a spacer while being freely accessible at the ouside of dispenser 1. Flange 4 has two shells 31, 32 freely protruding in opposite directions 62, 21. Shells 31, 32 adjoin each other via a ring-shaped end wall. From the inner circumference of narrower shell 32 and axially spaced from this end wall an annular disk-shaped flange member 33 protrudes. Member 33 rotary directly supports on the end face of flange 14 to thus axially tension flange 14 against base 6. Thus the end wall of flange 4 centeringly surrounds flange 14. Cover 13 is located totally within shell 32 and the end wall. The free end face of shell 23 forms a shoulder or pushing face 34 and the outside of the end wall forms a shoulder 35 between shells 31, 32. Shoulder 35 opposes shoulder 34 between which the blocking member 30 engages.

Base 6 has a neck 36 narrower than its barrel. Neck 36 or its outer circumference has a retaining or snap member, e.g. a circumference groove, spaced from the necks end face 38. On the inner circumference shell 31 has a correspondingly protruding complementary snap member 39. Two steeper flanks of members 37, 39 point in direction 61 and form the joint or connection 40, namely a resilient snap engagement, between dispenser 1 and base 6 while tensionally supporting against each other. End surface 38 surrounds the reservoir opening which is traversed by casing 8 by a gap spacing. For sealing, a seal 41 is inserted between end face 38 and the tensioning face of flange 14 facing face 38. Seal 41 is likewise axially tensioned or compressed. Seal 41 indicated dot-dashed sealingly contacts with axial or radial tension not only flange 14 and end face 38 but also the outer circumference of housing part 12, the inner circumference of shell 31 and the inner end face of the end wall of flange 4.

The interior space of base 6 is vented to compensate the drop in pressure resulting from drawing the medium. For this purpose a vent 42 bypassing casing 8 is provided with an angular fluid duct 43. At the inner circumference of shell 31 duct 43 has the longer axial duct branch 44. At the inside of the end wall of flange 4 duct 43 has the shorter branch 45. Duct 43 is formed by a groove in flange 4. This groove traverses the annular fastening member 39 which extends continuously annular up to the groove flanks. Seal 41 is pressed into branches 44, 45 radially or axially. Thus seal 41 tensionally contacts the groove bottom also in the transition zone between branches 44, 45. Seal 41 is non-permeable for liquids but permeable or semi-permeable for air. Thus seal 41 is simultaneously a filter, such as a germ filter. The air enters filter 41 axially in direction 61 from the free end of shell 31 through branch 44. Thereafter the air flows radially through filter 41 toward axis 10 to finally flow along the outside of casing 8 in direction 62 into reservoir 6. Reference is made to US patent application serial No. 09/387124 as regards further features and effects incorporated in the invention.

The integral blocking member 30 has a ring-shaped or partially ring-shaped locking body 46 extending over at least 180° to 310° and maximally over 350° about axis 10. Body 46 has two shells 47, 48 directly adjoining each other. The outer circumferential faces of shells 47, 48 translate smoothly into each other. The inner circumferential faces transit into each other via a blocking face 49. The thicker shell 47 forms between shoulders 34, 35 a blocking member. Therefore shoulders 34, 35 abut against blocking faces 49, 51 which face away from each other. Shell 48 envelopes shell 23 as a shield so tightly that shell 23 is prevented from becoming distended by jolting load. The space between faces 49, 51 corresponds roughly to half the working stroke of head 5, but may also be considerably greater. The outer circumferential faces of blocking member 30 or blocking body 46 and of shell 31 are the same in width.

The circumferential gap formed by the opposed ends of open ring body 46 is closed by a bridge or means 50 for preventing widening and distention. Shell or ring section 52 of bridge 50 is thinner than shell 48 and is offset relative to shell 48 radially outwardly about its thickness. Section 52 is integrally connected to the opposed end faces of body 46 via connecting links or nominal frangible points 53, or via hinge members, or the like. Links 53 are cross-sectionally weaker than section 52. Links 53 are located only at the downstream end of section 52, but are set back by this end relative to the downstream end of shell 48. Links 53 extend over less than half of the axial length of bodies 46, 50 and enable to pivot bridge 50 relative to body 46 about a tangential axis traversing both links 53.

Therefor bridge 50 has an upstream elongation of shell 52 to provide a release handle 56 jutting inclined away from shell 31. Handle 56 extends almost up to the plane of the free end face of shell 31 or up to the shoulder between neck and barrel of bottle reservoir 6. Thus handle 56 can be undergrasped by a finger nail and drawn outwardly while pivoting about links 53. Adjoining handle 56 section 52 supports against the outer circumference of shell 31, in case, radially tensioned. On pivoting links 53 are either severed off by torsional shear or one of links 53 enables bridge 50 to be pivoted about an axis parallel to axis 10 when only the other link 53 is severed. Then bridge 50 can be moved back into its closing position. Bridge 50 closes the opening or ring gap or insertion mouth 54 of body 46. This removal/insertion mouth 54 is used to radially withdraw blocking member 30 from dispenser 1.

Therefor blocking body 46 forms by its end radially resilient legs, the interspacing of which at gap 54 is considerably smaller than the diameter of the associated shell 32. These leg ends slide on shell 32 on removal. Thereby they primarily resiliently spread wide before then returning to their initial position. At the leg ends weblike flank juts 55 project radially outward from the outer circumference of blocking body 46 and extend only over the full length of blocking body 46. The opposing flanks of juts 55 bound mouth 54 funnel-shaped and radially diverge outwardly. Thus blokking body 46 can also be remounted onto shell 32 whereby the legs resiliently widen up before then clicking back into the blocking position. Bridge 50 does not have the blocking face 49. For pulling off and slipping on blocking body 46 has a handle 57 at that circumferential zone which faces away from mouth 54.

Member 30 and handle 22 are symmetrical to a common axial plane. Thus handle 56 protrudes according to FIG. 2 radially at one narrow side 28 and handle 57 protrudes radially at the other remote narrow side. Likewise in axial view blocking body 46 does not protrude over the length edges 27 or only significantly less than handles 56, 57.

Blocking member 30 is located in the vicinity of members or cams 58, 59 of withdrawal preventing means 61 which positively prevent body 5 from being removed from body 4. Annular cam or downstream end 58 of flange 4 protrudes outwardly from shell 32. Annular cam 59 protrudes beyond the inner circumference of shell 23 at the free end. When head 5 is moved from the rest position in direction 62 cams 59 abut on cam 58. In the cited axial plane of blocking member 30 the radial height of cams 58, 59 is reduced or totally interrupted. When head 5 is mounted in direction 62 cams 58, 59 ride past each other by radial resiliency of shells 23, 32 until they click back into their function position as a snap connector. Cam 59 is located partly or fully within shell 48.

Piston unit 9 requires axial running forces to overcome the running resistance which may increase with increasing stroke due to a return spring located in casing 8. To produce connection 26 an axial connecting force is needed to overcome the connecting resistance of pinch fit 26. To bring flange cap 31 or member 39 into the cited joint engagement with base 6 an axial jointing force is needed which overcomes the jointing resistance. To produce joint 40 between dispenser 1 and base 6 the dispenser 1 is grasped by a pressing tool so that its pressing faces support against at least one of the cited driving faces 22. The dispenser 1 is then linearly impacted onto neck 36 in direction 62 with this tool. Thereby head 5 primarily executes the partial stroke up to abutment on blocking face 49, the jointing force then being transmitted to flange 4 solely by shell 47.

Due to the foregoing partial stroke the return spring is stronger pretensioned so that by this spring casing 8 is already firmly tensioned against end face 38 or seal 41 with flange 4 before connection 40 is produced. After this flange 4 still executes an axial travel relative to casing 8 until attaining its jointing position. Flange 4 and casing 8 or its associated part 12 or 13 may also be integral with each other. For executing a discharge stroke blocking member 30 is removed or released in the cited way and for subsequent locking member 30 is returned. The partial travel of the working stroke until stopped by the blocking face 49 is selected so that the outlet valve of pump 7 is not opened thereby. On the return stroke from this intermediate position, medium is drawn from reservoir 6 into the pump chamber via inlet 11. Thus medium is able to emerge from medium outlet 16 already on the next or next thereafter pump stroke.

In FIGS. 6 to 8 blocking body 46 circumferentially extends uninterrupted as a closed annular shell of constant thickness while maximally reaching up to shell 23 or the outside thereof. Blocking member 30 connects to pushing face 34 via connecting links 53 which are circumferentially distributed about the circumference with interspacings and solely transmit the cited jointing force to ring member 30. In axial view handle 56 juts over length side 27 and is located in the vicinity of a nominal frangible or weak zone of member 30. When handle 56 is tiltedly drawn radially outward this frangible element tears and member 30 can be removed as an open tape. The shell thickness of locking body 46 i s less than that of shell 23. Body 46 is axially spaced from shell 23 by a cleft. This tiny cleft is bridged only by links 53.

In FIG. 9 head 5 is already blocked in the rest position. In this position faces 49, 51 contact faces 34, 35 with zero clearance or with light axial tension. For jointing bodies 4, 5 the blocking member 30 and at least one of bodies 4, 5, particularly flange 4 in FIGS. 1 and 9 and head 5 in FIG. 6, may commonly be a preassembled unit. In addition, member 30 fitted to dispenser 1 is rotary about axis 10 relative to both bodies according to FIGS. 1 and 9 and together with body 5 relative to body 4 according to FIG. 6.

Bodies 4, 5 also over the full stroke may be prevented from mutually rotating, e. g. by cams 58, 59 or by the associated circumferential faces of shells 23, 32 having riding flats which are offset radially inwardly relative to the connecting circumferential faces.

It is to be noted that like parts in all embodiments are identified by like reference numerals and thus all passages of the description apply accordingly for all embodiments. Each feature of each embodiment may be provided in any other embodiment additionally or in combination. The size relationships as shown are favorable for many applications for an overall length of the dispenser 1 of max. 100 or 80 mm. The effects and properties may be precisely or merely substantially or roughly as described or may even greatly deviate therefrom for corresponding applications.

What is claimed is:

1. A dispenser for medium comprising:
    dispenser units (2,3) including an actuating head (5) for actuating said dispenser (1) and a flange (4) for being fastened to a medium reservoir base (6) by a snap action under a snap action force, said head (5) including a media duct (15) connected to a media outlet (16) and being movable relative to said flange (4) under an actuation force from a rest position to an actuated end position, said head (5) including a driving face (22), for exerting said snap action force to said head and a locking member (20) connecting said flange (4) to the base (6) by supporting said head (5) against said flange (4) before said head (5) reaches said actuated end position whereby the snap action force is transmitted directly from the head to the flange, said locking member (20) being removable from the dispenser for allowing the dispenser to be actuated.

2. The dispenser according to claim 1, wherein said locking member (20) includes a blocking member (30) with a locking body (46) directly contacting at least one of said dispenser bodies (4, 5) by a blocking face (49, 51) of said locking body (46).

3. The dispenser according to claim 1, wherein said flange (4) includes a counter face (35) supporting said head (5) when pushed towards the base (6), said flange (4) including a downstream end (58) located downstream of said counter face (35).

4. The dispenser according to claim 1, wherein said head (5) includes an upstream end including an inner circumference, said upstream end including a pushing face (34) for pushing said flange (4) against the base (6) with said inner circumference hieing bare.

5. The dispenser according to claim 2, wherein said blocking member (30) extends over at least 310° about a middle axis of said base, means (50) being included for positively preventing said blocking member (30) from being widened.

6. The dispenser according to claim 2, wherein said blocking member (30) is annular over substantially 360° about a middle axis of said base, said blocking member (30) including a ring section (52) removable from said locking body (46) to form a ring gap (54), said ring section (52) connecting to said locking body (46) via a connecting link (53).

7. The dispenser according to claim 2, wherein said blokking member (30) includes means (50) for preventing distention, said preventing means (50) being disengagable with a release handle (56).

8. The dispenser according to claim 2, wherein said blokking member (20) includes remote ends, said blocking face (49) being spaced from at least one of said remote ends, said blocking member (30) including a clamp for preventing at least one of said dispenser bodies (4, 5) from being radially deformed.

9. The dispenser according to claim 2, wherein said blokking member (30) and at least one of said dispenser bodies (4, 5) commonly provide a preassembled unit, said blocking member (30) connecting to at least one of said dispenser bodies (4, 5) via at least one nominal frangible point (53).

10. The dispenser according to claim 2, wherein said blokking member (30) includes an insertion mouth (54) for releasing at least one of said dispenser bodies (4, 5), said insertion mouth (54) being bounded by at least one flank jut (55), said blocking member (30) defining a first wall thickness and said at least one flank jut (55) defining a second wall thickness differing from said first wall thickness.

11. The dispenser according to claim 1, wherein said flange (4) is to be brought into an axially locked joint with said base (6), said flange (4) bounding a fluid duct (43).

12. The dispenser according to claim 2, wherein said blokking member (30) has varying axial extensions.

13. The dispenser according to claim 2 and further defining an axial plane of said blocking member (30), wherein said blocking member (30) has varying radial extensions along said axial plane.

14. The dispenser according to claim 2, wherein at least one of
   said blocking member (30), and
   said head (5)
   circumferentially envelopes said flange (4).

15. The dispenser according to claim 2, wherein said blokking member (30) permits to displace said head (5) relative to said flange (4) over an idle path with said locking body (46) engaging at least one of said dispenser bodies (4, 5).

16. The dispenser according to claim 2, wherein said locking body (46) includes an internal projection including said blocking face (49).

17. The dispenser according to claim 2, wherein said locking body (46) defines a width extension and a length extension at the most as big said width extension.

18. The dispenser according to claim 2, wherein said blocking member (30) juxtaposes said base (6) transverse to a middle axis of said base.

19. The dispenser according to claim 2 and further including means (60) for preventing said head (5) from being withdrawn from said flange (4), wherein said blocking member (30) circumferentially shields said preventing means (60).

20. The dispenser according to claim 2 and further including a release handle (56) for gripping said blocking member (30), wherein said base (6) includes a shoulder closely directly opposing said release handle (56).

21. A method for mounting a medium dispenser to a reservoir, the dispenser including dispenser units having an actuating head for actuating said dispenser under an actuation force by relative movement of the head and the reservoir from a rest position to an actuated position, a flange and snap action means, comprising:
   interposing a blocking member between the head and the flange;
   exerting snap action force on driving faces provided at the head to move the head relative to the reservoir until the snap action means snap on said reservoir, the blocking member preventing movement of the head to the actuated position of the dispenser while the snap action force is acting; and
   removing the blocking member from the dispenser to allow unrestricted actuation of the dispenser to its actuated position.

* * * * *

UNITED STATES PATENT AND TRADEMARK OFFICE
CERTIFICATE OF CORRECTION

PATENT NO. : 6,352,181 B1
DATED : March 5, 2002
INVENTOR(S) : Thomas Eberhard and Anton Breyer It is certified that error appears in the above-identified patent and that said Letters Patent is hereby corrected as shown below:

Column 1,
Line 66, "flange. (When" should be -- flange. When --;

Column 2,
Line 1, "repeatable.) In" should be -- repeatable. In --;

Column 5,
Line 23, "blokking" should be -- blocking --;
Line 24, "legs resilienty" should be -- legs resiliently --;
Line 51, "restistance" should be -- resistance --;

Column 7,
Line 19, "hieing bare." should be -- lying bare. --;
Lines 33, 37, 43, and 49, "blokking" should be -- blocking --;

Column 8,
Lines 2 and 14, "blokking" should be -- blocking --.

Signed and Sealed this

Twenty-second Day of April, 2003